United States Patent [19]
Nanjo

[11] Patent Number: 5,302,988
[45] Date of Patent: Apr. 12, 1994

[54] STEREOSCOPIC RETINAL CAMERA INCLUDING VERTICALLY SYMMETRICAL APERTURES

[75] Inventor: Tsuguo Nanjo, Toyohashi, Japan

[73] Assignee: Nidek Co., Ltd., Japan

[21] Appl. No.: 37,653

[22] Filed: Mar. 17, 1993

[30] Foreign Application Priority Data

Mar. 31, 1992 [JP] Japan .................. 4-108502
Sep. 30, 1992 [JP] Japan .................. 4-287001

[51] Int. Cl.$^5$ .................. G03B 29/00; A61B 3/10; A61B 3/14
[52] U.S. Cl. .................. 354/62; 354/112; 351/206; 351/213; 351/214; 351/221
[58] Field of Search ........ 354/62, 110, 112, 113, 354/115, 117; 351/205, 206, 214, 213, 221

[56] References Cited

U.S. PATENT DOCUMENTS 4,715,703 12/1987 Cornsweet et al. .................. 351/205

FOREIGN PATENT DOCUMENTS 4-71528 3/1992 Japan .

OTHER PUBLICATIONS

"A New Camera for Stereoscopic Fundus Photography", David D. Donaldson, Archives of Ophthalmology, vol. 73, pp. 253-267, Feb., 1965.

"Stereoscopic Retinal Camera", Mizuo Matsui, Ophthalmology, vol. 19, No. 10, 1977 (with abstract).

Primary Examiner—M. C. Gellner
Assistant Examiner—J. K. Han
Attorney, Agent, or Firm—Parkhurst, Wendel & Rossi

[57] ABSTRACT

A stereoscopic retinal camera capable of photographing the stereoscopic picture of the fundus by dividing a light beam reflected by the fundus into two light beams and transmitting the two light beam respectively along the light paths of separate image forming optical systems, the stereoscopic retinal camera comprising photographing diaphragms having two apertures for dividing the light beam reflected by the fundus, disposed in a conjugate relation with respect to the pupil of the examinee's eye through an objective lens so that a photographing image of the fundus of the eye may appear stereoscopic properly based on a stereobase determined on the pupil, the respective apertures of photographing diaphragms having a longer vertical length than a width.

14 Claims, 7 Drawing Sheets

FIG. 1

Prior Art

STEREOSCOPIC RETINAL CAMERA INCLUDING VERTICALLY SYMMETRICAL APERTURES

BACKGROUND OF THE INVENTION

1. Field of the Invention

The present invention relates to a stereoscopic retinal camera, and more particularly to a stereoscopic retinal camera comprising a photographing diaphragm preferable to photograph the eye of a small pupil diameter, and to photograph without using the mydriatica, namely, under non-mydriasis of the pupil.

2. Description of Related Art

Conventionally, simultaneous stereoscopic retinal camera comprises a photographing diaphragm disposed in a position substantially conjugated with the pupil of the examinee's eye, which separates the luminous flux reflected by the fundus of the eye into two luminous flux, and an image forming optical system disposed on each optical path of the two luminous flux to photograph an image of the fundus focused on a photographing film through the image forming optical system by a flashlight. The almost conventional photographing diaphragm are small circle or round in shape.

A photographing diaphragm in the retinal camera is arranged substantially conjugate with the pupil of the examinee's eye, and also there is known from experience that the stereobase being not less than 3 mm may give a satisfactory stereoscopic vision in the stereoscopic retinal observation, the stereobase being a central distance between a right and left diaphragms on a surface of the pupil the satisfactory stereoscopic vision may be obtained in the stereoscopic retinal observation when the stereobase being a central distance between a right and a left diaphragms on a surface of the pupil.

When trying to photograph by such a stereoscopic retinal camera without the mydriasis, one flash for photographing the fundus will make the examinee's eye miosis, then, the sequential photographing can not be continued. Therefore, the condition requested for the non-mydriasis photographing is to photograph certainly by one flash. It is also desired that a pupil diameter capable of being photographed is the shortest possible diameter. However, it is necessary in the stereoscopic photographing that two photographing luminous flux are taken out respectively from right and left sides of the optical axis on the pupil, whereby the shortest pupil diameter necessary to produce the luminous flux will become larger. Thus, non-mydriasis photographing needing the capacity to coordinate with respect to a small pupil diameter is considered unfit for a stereoscopic retinal camera.

Figure 1:
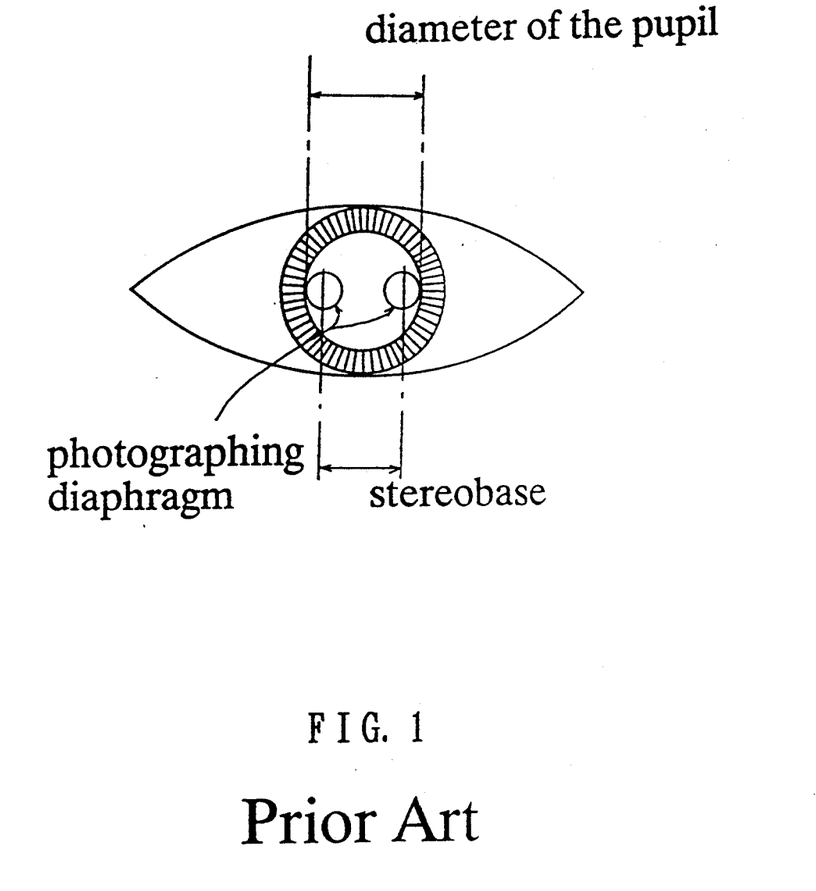
FIG. 1 is a schematic view of explaining conceptually a photographing method using a conventional photographing diaphragm.

For example, when a stereobase on the pupil is 3 mm and a pupil of the a $\phi 4$ mm diameter, the luminous flux to be transmitted into the pupil can have only 1 mm diameter through the conventional circular diaphragm as shown in FIG. 1, and the light quantities will be $\frac{1}{2}.25$ based on that a diameter of luminous flux in a standard retinal camera is about $\phi 1.5$ mm.

A relation between visual resolution ($\psi$) and pupil diameter (d) will be given in accordance with the following formula: $\sin \psi = 1.22 \times \lambda/d$, where $\lambda$ represents a wavelength of luminous flux, and then, $\psi$ is about 1.77° ($\lambda = 550$ nm) when $d=1$, about 1.18° when $d=1.5$. It is thus understood that the visual resolution ($\psi$) lowers by about one-third, so that the vision quantity of the fundus can not be preferably obtained.

As described above, when keeping the stereobase 3 mm and using a small circular diaphragm in the conventional apparatus, it will be necessary to expand the pupil of the examinee's eye correspondingly to heighten the resolving power of photographing by extending the diaphragm, or to introduce much quantity of the light. Thus, if a standard diaphragm diameter of a retinal camera is about $\phi 1.5$ mm and the stereobase is 3 mm, the pupil needs to have a diameter of 4.5 mm and more, namely, it is not able to photograph the fundus of the eye when the pupil diameter is less than 4.5 mm.

It is said that a stereoscopic retinal camera is very useful in diagnosing a case of glaucoma, particularly the gradual change in progressing condition thereof, but the use of mydriatica is prohibited because the mydriatica causes the deterioration of condition dependent upon the progressing condition. Therefore, the stereoscopic retinal camera has limits of the use also in a case for which the retinal camera is very useful.

SUMMARY OF THE INVENTION

The present invention has been made in view of the above circumstances and has an object to overcome the above problems and to provide a stereoscopic retinal camera capable of photographing the fundus of the eye stereoscopically by keeping the stereobase and if a pupil diameter being less than $\phi 4.5$ mm by keeping the stereobase.

Another object of the present invention is providing a stereoscopic retinal camera capable of having a high visual resolution and keeping the quantity of light sufficiently to obtain a preferable picture plane of a photographing image of the fundus.

Further object of the present invention is providing a stereoscopic retinal camera of non-mydriasis type capable of photographing the fundus preferably without using the mydriatica.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, a stereoscopic retinal camera capable of photographing the stereoscopic picture of the fundus by dividing a light beam reflected by the fundus into two light beams and transmitting the two light beam respectively along the light paths of separate image forming optical systems, the stereoscopic retinal camera of this invention comprises photographing diaphragms having two apertures for dividing the light beam reflected by the fundus, disposed in a conjugate relation with respect to the pupil of the examinee's eye through an objective lens so that a photographing image of the fundus of the eye may appear stereoscopic properly based on a stereobase determined on the pupil, the respective apertures of photographing diaphragms having a longer vertical length than a width.

In another aspect of the present invention, a stereoscopic retinal camera comprises illumination optical system for illuminating the observing illumination light and the photographing illumination light, photographing optical system for transmitting the luminous flux reflected by the fundus onto a photographing film, observation optical system for transmitting the luminous flux reflected by the fundus onto an imaging device, the photographing optical system and the observation optical system use partially the common light path comprising a photographing diaphragm, the photographing diaphragm being provided with a pair of apertures to divide the luminous flux reflected by the fundus for the stereoscopic observation through the observation optical system and for stereoscopic photographing through the photographing optical system, the respective apertures of the photographing diaphragm shaping like a drum which has longer vertical length than its width.

By using the stereoscopic retinal camera of the present invention, it is possible to photograph stereoscopically the fundus of the eye without mydriasis of the pupil.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

A detailed description of one preferred embodiment of a stereoscopic retinal camera embodying the present invention will now be given referring to the accompanying drawings.

Figure 2:
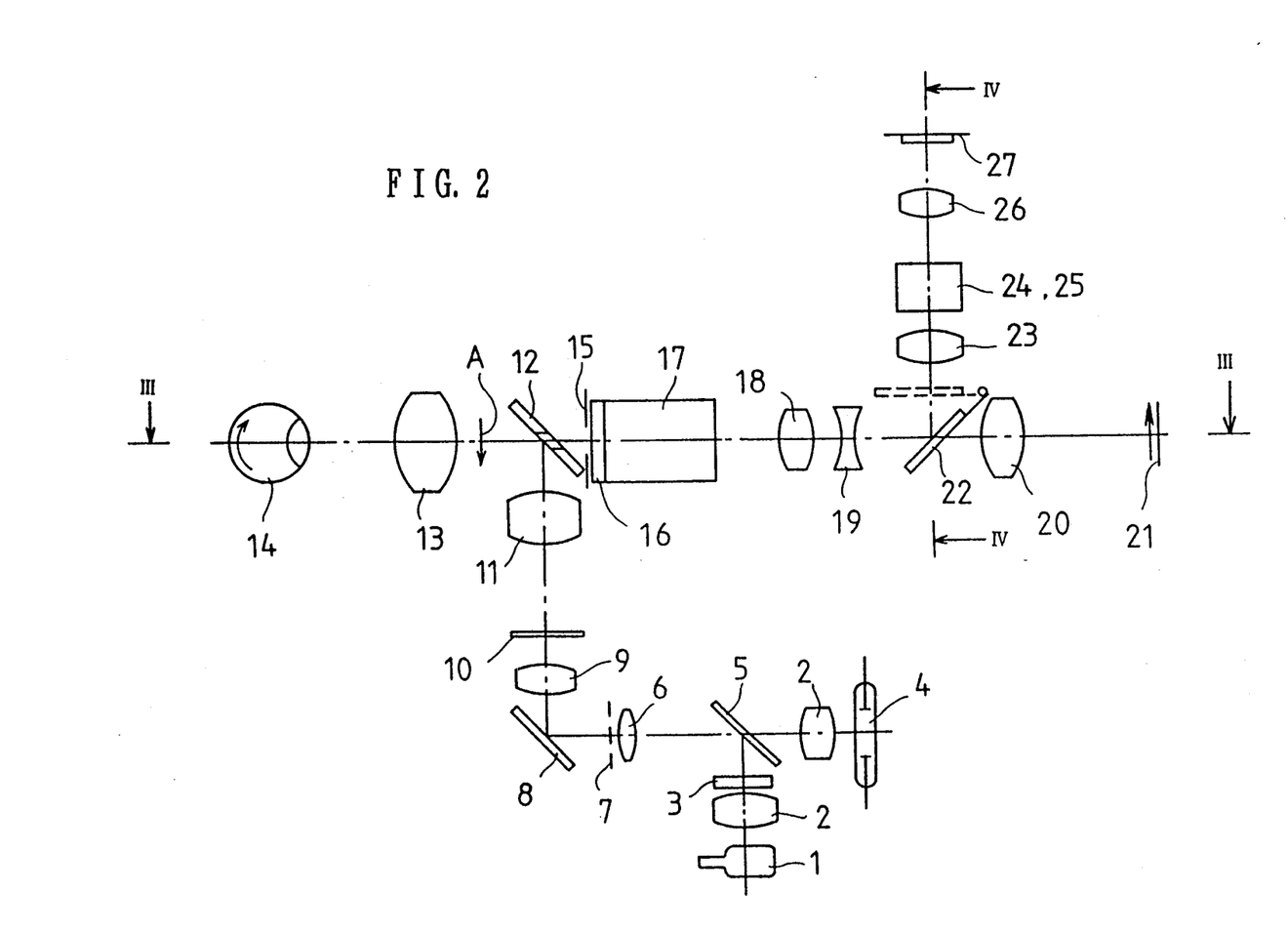
FIG. 2 is a diagrammatic side view of the optical systems of a stereoscopic retinal camera in a first embodiment according to the present invention.
Figure 3:
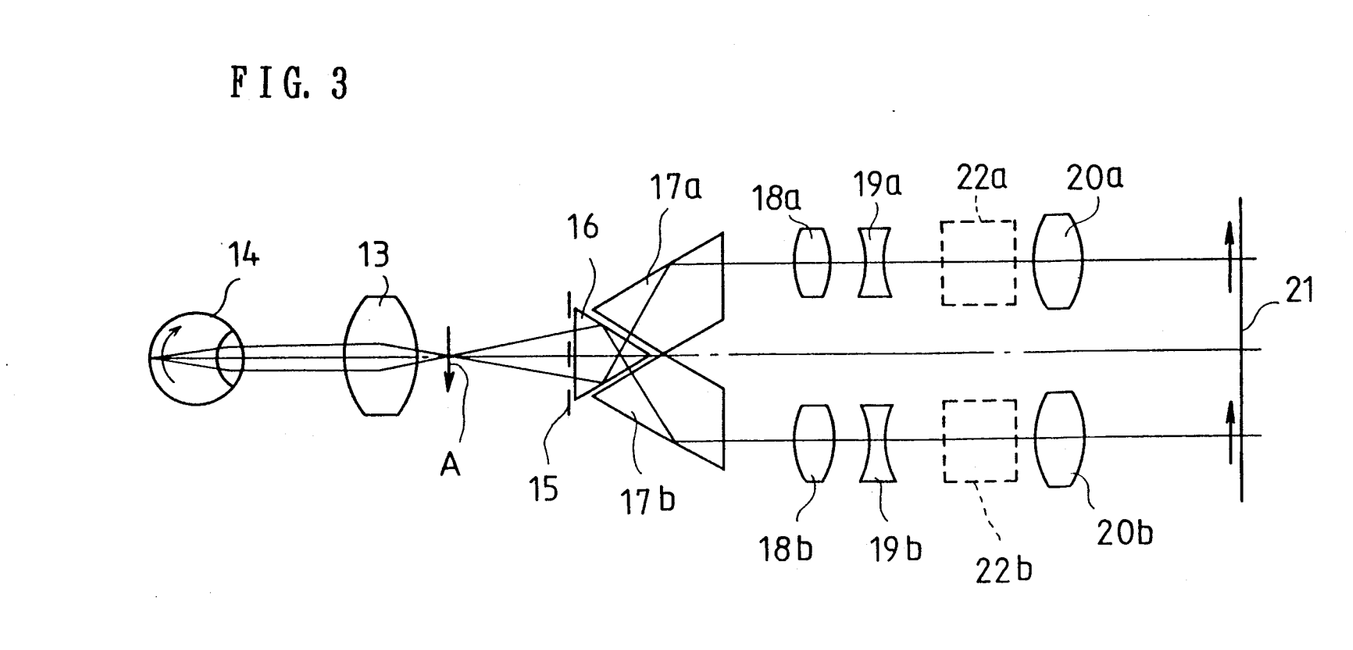
FIG. 3 is a diagrammatic sectional view on line III—III of the optical systems of the stereoscopic retinal camera of FIG. 2.
Figure 4:
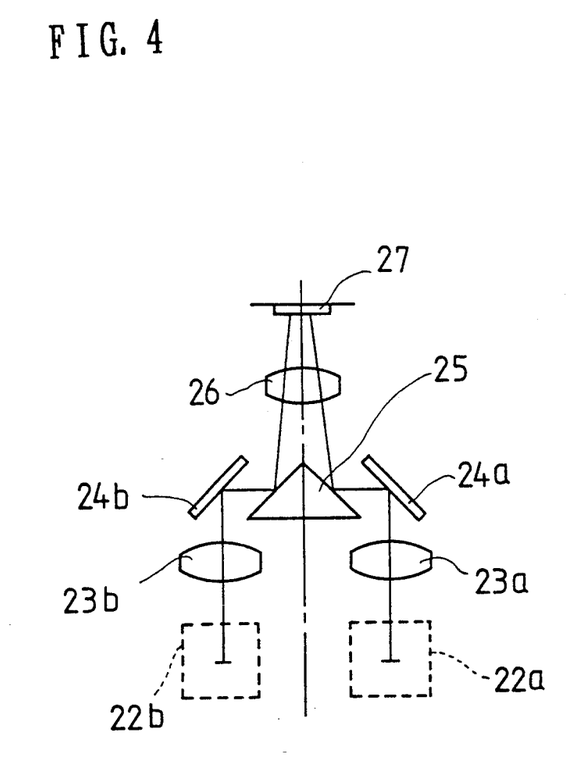
FIG. 4 is a diagrammatic sectional view on line IV—IV of the optical systems of the stereoscopic retinal camera of FIG. 2.

In FIG. 2, there is shown a stereoscopic retinal camera in a first embodiment according to the present invention, which comprises an illumination optical system, a photographing optical system and an observation optical system. FIG. 3 shows the photographing optical system on line III—III of FIG. 2, and FIG. 4 shows the observation optical system on line IV—IV of FIG. 2.

ILLUMINATION OPTICAL SYSTEM

The illumination optical system of the stereoscopic retinal camera comprises an observing illumination optical system and a photographing illumination optical system.

The observing illumination optical system comprises a halogen lamp 1 which is a light source of observing illumination light, a condenser lens 2 for condensing the light beam emitted from the halogen lamp 1, an infrared filter 3 capable of transmitting only the infrared light by removing the visible light element of observing illumination light, a beam splitter 5 capable of reflecting the infrared light, but transmitting the visible light, a condenser lens 6, a ring slit 7 which is a ring type aperture diaphragm, a mirror 8 for deflecting the optical path, relay lenses 9 and 11 of illumination optical system, an index plate 10 to eliminate the detrimental light, a perforated mirror 12 included centrally an aperture to transmit the photographing luminous flux, and an objective lens 13. The index plate 10 is provided with a small black point on its center portion.

Figure 5:
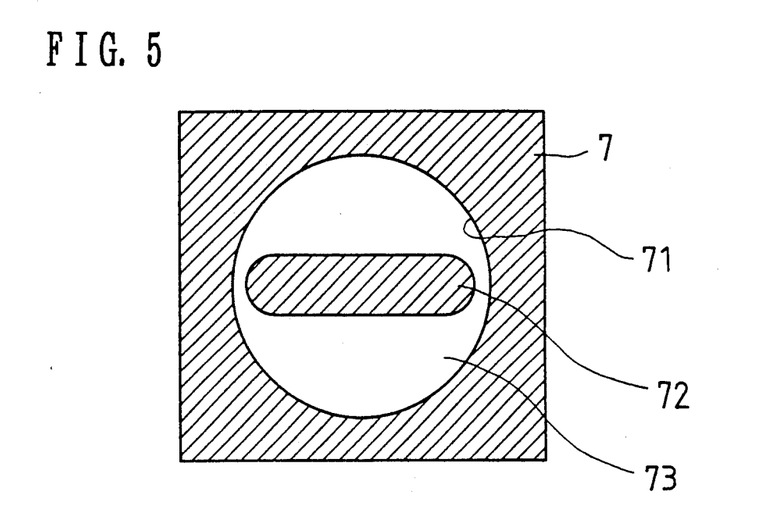
FIG. 5 is a schematic view of a ring slit 7 of FIG. 2.

As shown in FIG. 5, the ring slit 7 has an elliptic shade 72 in a circular aperture 71 to constitute a light transmitting slit 73 of a ring form.

The light beam emitted from the halogen lamp 1 is transmitted toward the examinee's eye 14 to illuminate the fundus through the infrared filter 3, the beam splitter 5, the condenser lens 6, the ring slit 7, the mirror 8, the relay lens 9, the index plate 10, the relay lens 11, the perforated mirror 12, and the objective lens 13.

The photographing illumination optical system comprises a flash lamp 4, a condenser lens 2' for condensing the light beam emitted from the flash lamp 4, and shares the beam splitter 5, the condenser lens 6, the ring slit 7, the mirror 8, the relay lens 9, the index plate 10, the relay lens 11, the perforated mirror 12, and the objective lens 13 respectively with the observing illumination optical system mentioned above. The halogen lamp 1 for observation light and the flash lamp 4 for photographing light are disposed at a conjugate position each other through the condenser lenses 2 and 2'. Both luminous flux emitted from the halogen lamp 1 and the flash lamp 4 are compounded into the coaxial luminous flux through the beam splitter 5 to illuminate the ring slit 7. The luminous flux transmitted through the ring slit 7 forms an intermediate image close to the aperture of the perforated mirror 12 through the relay lenses 9 and 11, and then is reflected by the perforated mirror 12 to be coaxial with the optical axis of the objective lens 13. The image of the ring slit 7 is subsequently formed close to the pupil on the examinee's eye 14 and diffuses into the examinee's eye to illuminate the fundus.

PHOTOGRAPHING OPTICAL SYSTEM

Figure 6:
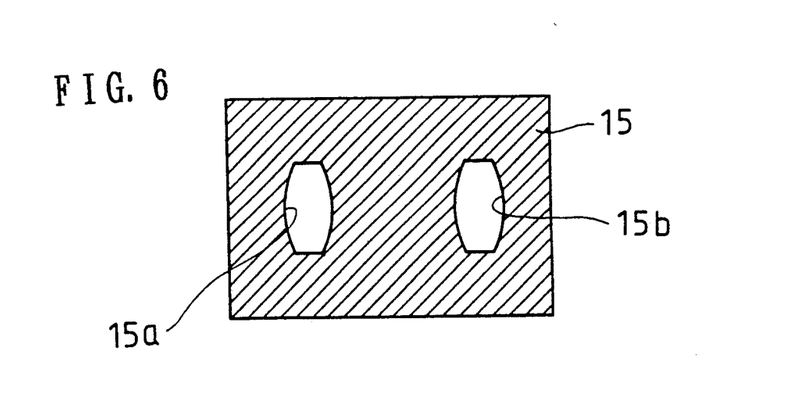
FIG. 6 is a schematic view of a two-hole diaphragm 15 of FIG. 2.

The photographing optical system comprises the objective lens 13 shared with the illumination optical system, the perforated mirror 12, a two-hole diaphragm 15 for splitting the light beam into two light beams for stereoscopic observation and photographing, light beam splitting prisms 16 and 17, a relay lens 18, a focusing lens 19, an image formation lens 20. The two-hole diaphragm 15 is provided with a pair of drum-shaped apertures 15a and 15b as shown in FIG. 6, these apertures 15a and 15b both have a symmetrical form and a longer length than its width to extend an aperture area.

The light beam splitting prism 16 interchange a right light beam and a left light beam each other, and the light beam splitting prisms 17 collimate the two light beams so that the collimated light beams pass along two parallel paths separated from each other by a predetermined distance. The focusing lenses 19a and 19b are movable along the optical axis of the focusing lenses 19a and 19b so as to be adjusted according to the refracting power of the eye 14 to focus the image of the fundus on the film 21.

The light beam reflected by the fundus of the eye 14 is irradiated onto the film 21 through the objective lens 13, the perforated mirror 12, the two-hole diaphragm 15, the light beam splitting prisms 16 and 17, relay lenses 18 (18a, 18b), focusing lenses 19 (19a, 19b) and image forming lenses 20 (20a, 20b) to form the image of the fundus on the film 21.

Figure 7:
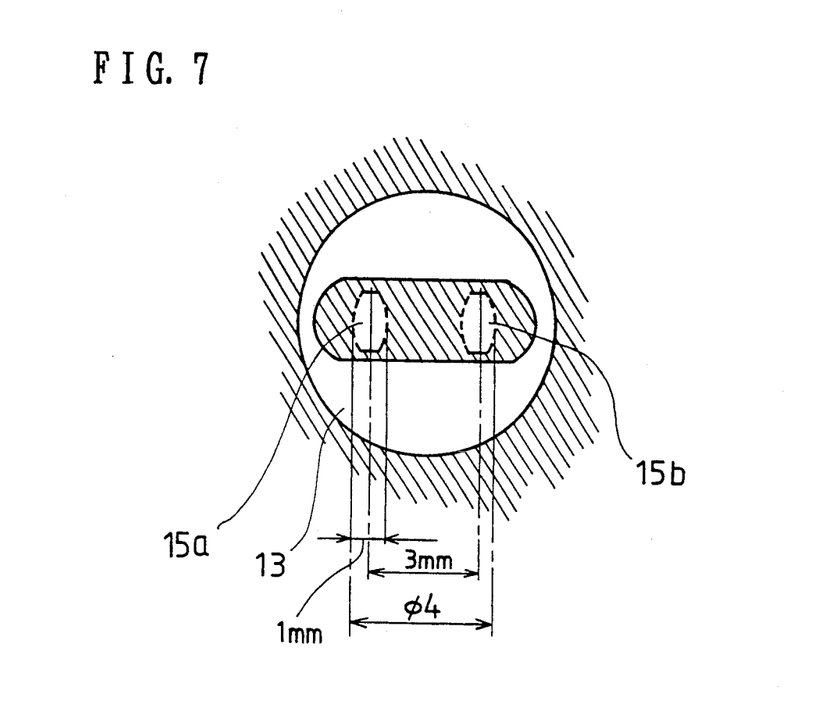
FIG. 7 is a schematic view of putting the ring slit of FIG. 5 over the two-holes diaphragm of FIG. 6.

The two-hole diaphragm 15 is explained as follows. The two-hole diaphragm 15 is disposed so as to be conjugate with the pupil of the eye 14 through the objective lens 13, so that the luminous flux separated on the pupil for stereoscopic photographing will be compounded at A point, further split into two luminous flux again. Namely, the range of area of photographing luminous flux substantially depends upon the area on the pupil. Because the image of the ring slit 7 is formed close to the pupil on the examinee's eye, the ring slit 7 and two-hole diaphragm 15 are disposed substantially conjugate each other on the pupil. Therefore, when the ring slit 7 is put over the two-hole diaphragm 15 on the pupil, respective images of an slit 73 of the ring slit 7 and apertures 15a, 15b appear as shown in FIG. 7.

The distance between each base through which the right and the left luminous flux transmit is fixed to the length capable of providing a substantial stereoscopic image. To realize the capacity for corresponding with a small pupil (less than 4 mm in diameter), the luminous flux passed through the apertures 15a and 15b of the two-hole diaphragm 15 both have drum-shaped cross section respectively, each of them having a longer vertical length than its width so that the luminous flux have the same area as that of the luminous flux having a 1.5 mm diameter capable of keeping the normal photographing performance of the retinal camera, i.e. $0.75 \times 0.75 \times \pi$ mm$^2$. Additionally, the two-diaphragm 15 is constructed so that a center distance between both apertures 15a and 15b is 3 mm, a distance between each outside diameter edge of the apertures 15a and 15b is 4 mm.

The photographing luminous flux having a cross section in the form as mentioned above will have the calculative sectional area of 1.8 mm$^2$, as a result, the photographing performance can be obtained equally when the luminous flux of 1.5 mm diameter has the area of 1.77 mm$^2$. As described above, each apertures 15a, 15b of two-hole diaphragm 15 are constituted to keep the area balance so that the stereobase may be not different from the optical axis, particularly, the area balance may be kept by that both apertures in this embodiment are symmetrically in shape.

Figure 8:
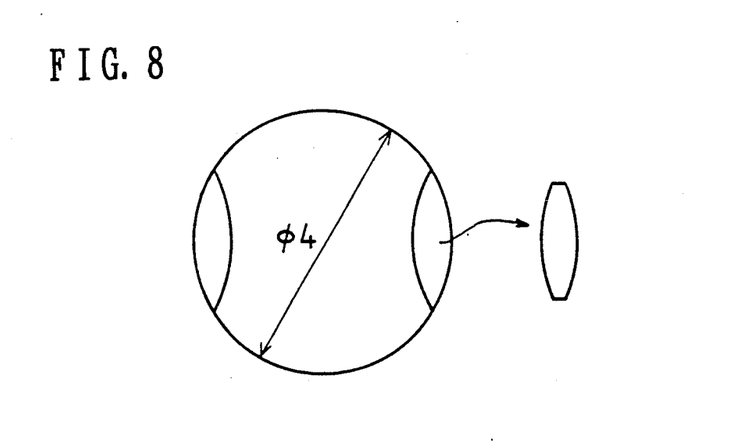
FIG. 8 is a schematic view of explaining apertures of two-holes diaphragm.

While the aperture 15a and 15b of the two-hole diaphragm 15 in the present embodiment are shaped like a drum by cutting top and bottom portions of figure shown in FIG. 8, the area of aperture will change little in comparison with FIG. 8 and the illumination light transmitting quantity from upper and lower sides within a diameter of 4 mm can be increased while restraining the two-hole diaphragm 15 from interfering in a slit image of the ring slit 7. The aperture form of the diaphragm 15 may be changed within the change of area being as slight as no problem occurs on practical use.

The fundus illuminating luminous flux by the ring slit 7 is transmitted through the part without interfering with the two photographing luminous flux on the pupil, specifically, through mainly the upper and lower part of the two luminous flux. The ring slit 7 is designed so that the light quantity through the ring slit 7 may be introduced into the fundus of the eye as much advantageously as the mydriasis diameter is wide. And also, in case that the pupil diameter of the examinee's eye is enough wide, it is possible to photograph with the full light quantity by using the ring slit 7.

In the above photographing optical system, referring to FIG. 3, the light beam reflected by the fundus of the eye 14 is focused at a point A in an inverted image by the objective lens 13, passes through the opening of the perforated mirror 12, and is splitted into two light beams through the two-hole diaphragm 15. The two light beams become parallel luminous flux through the light beam splitting prisms 16 and 17 (17a and 17b), pass through relay lenses 18 (18a and 18b), focusing lenses 19 (19a and 19b) and image forming lenses 20 (20a and 20b), thereby the right and left images of the fundus are formed on the film 21 respectively.

OBSERVATION OPTICAL SYSTEM

The observation optical system and the photographing optical system use the components between the objective lens 13 and the return mirror 22 in common. That is, the observation optical system comprises the objective lens 13, the perforated mirror 12, the two-hole diaphragm 15, the light beam splitting prisms 16 and 17 (17a, 17b), the relay lenses 18 (18a, 18b), the focusing lenses 19 (19a, 19b) and return mirrors 22 (22a, 22b) disposed between the focusing lenses 19 and 20 on the light path of the photographing optical system, additionally relay lenses 23 (23a, 23b), mirrors 24 (24a, 24b) for deflecting luminous flux toward the inside so that a distance between the luminous flux may be shorter, triangle mirror 25 for deflecting the luminous flux toward the predetermined direction to coordinate/adjust two right and left images, image forming lens 26, TV camera imaging element 27 such as CCD and the like sensitive to the infrared area.

When observing the fundus, the return mirrors 22 (22a and 22b) disposed on the light path of the photographing optical system are set on the light path to reflect the observation light beam reflected by the fundus, alternatively move out the light path to pass the photographing light beam when photographing.

The observation light beam reflected by the fundus and passed through the components from the objective lens 13 through the focusing lenses 19a and 19b are reflected by the return mirrors 22a and 22b set on the optical path toward relay lenses 23a and 23b, and transmitted toward the image forming lens 26 through relay lenses 23a, 23b, mirrors 24a, 24b, the triangle lens 25. The observation image is then formed on an imaging element 27 in a conjugate relation with the film 21.

When observing the fundus, the fundus of the eye is illuminated by the invisible light passed through an infrared filter 3 of the luminous flux emitted from a halogen lamp 1. Alternatively, when instantaneous photographing, a flash lamp 4 is turned on synchronously with the return mirrors 22 moving out, so that the full quantity of light can be introduced to photograph.

Figure 9:
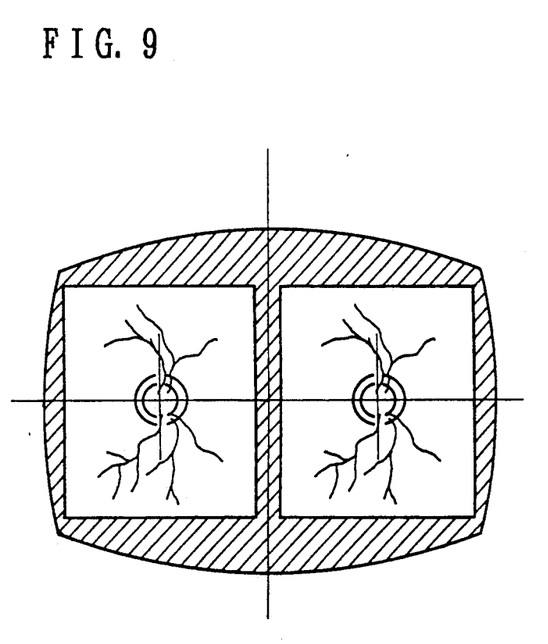
FIG. 9 is a schematic view of an example of TV monitor screen display.

An example of TV monitor screen for displaying a pair of picture images taken by TV camera is shown in FIG. 9, these right and left picture images will be used for stereoscopic photographing.

Although a TV camera and a TV monitor are employed in this embodiment, various modifications are convenient for operation, for example, of using exclusive TV cameras for right and left respective images and sharing only a TV monitor through an image composing circuit, or using plural TV monitors.

The operation of the stereoscopic retinal camera thus constructed will be described hereinafter.

The stereoscopic retinal camera is mounted on a movable table which is moved relative to a fixed table by a sliding mechanism. The examinee's head is held on a head support fixed to the fixed table, and the halogen lamp 1 is turned on to illuminate the examinee's eye 14 by the invisible infrared light. In case of photographing the fundus of the eye, the observer operates the sliding mechanism to align the stereoscopic retinal camera with the eye 14 so that the fundus is illuminated properly in proper position, while looking at an observation image appeared on TV monitor (referring to FIG. 9). When the alignment is substantially adjusted, each of right and left images of the fundus can be observed on TV monitor as shown in FIG. 9.

Additionally, the observer settles the visual field after adjusting the alignment fine, then a conventional alignment index and the like may be also used, and turns the focusing knob (not shown) to focus the focusing lenses 19a and 19b and makes the finest adjustment of the alignment of the image of the ring slit 7 with the pupil of the eye 14 (the focus index and the like may be also used).

After the operations for aligning the image of the ring slit 7 with the pupil of the eye 14 and for focusing the focusing lenses 19a and 19b have been completed, a shutter release button is depressed. Then, the return mirror 22 is lifted up to a position indicated with a broken line and the xenon flash lamp 4 flashes synchronously to form the image of the fundus on the film 21 with the full quantity of light.

The automatic operations except manual operations of the stereoscopic retinal camera are controlled by the control system including the microcomputer and the like mounted in the apparatus.

The examinee's eye 14 ordinary reacts to a regular light beam emitted from the xenon flash lamp 4, and will be miosis, but photographing an image of the fundus will have been finished before then. The photographing operation is performed by illuminating the fundus with the invisible illumination light, while utilizing the natural mydriasis of the pupil of the eye occurred in the dark. Therefore, the photographing with a stereoscopic retinal camera is performed in a darkroom.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A stereoscopic retinal camera capable of photographing a stereoscopic picture of a fundus by dividing a light beam reflected by the fundus into two light beams and transmitting the light beams respectively along light paths of right and left image forming optical systems, said stereoscopic retinal camera comprising:
    a photographing diaphragm, including two apertures for dividing the light beam reflected by the fundus into the two light beams that are respectively transmitted along the light paths of the right and left image forming optical systems, disposed in a substantially conjugate relationship with respect to a pupil of an examinee's eye through an objective lens so that a photographing image of the fundus of the eye may appear stereoscopic properly based on a stereobase determined on the pupil; wherein
    each aperture of the photographing diaphragm has a longer vertical length than width, and is substantially symmetrical in shape about a vertical central axis.

2. A stereoscopic retinal camera according to claim 1, wherein the apertures of the photographing diaphragm have an arc substantially in accordance with a diameter of an image of a pupil of an examinee's eye projected on the photographing diaphragm.

3. A stereoscopic retinal camera according to claim 2, wherein the pupil is about 4 mm in diameter.

4. A stereoscopic retinal camera according to claim 1, wherein each aperture of the photographing diaphragm has an arc substantially in accordance with a diameter of an image of a pupil of an examinee's eye projected on the photographing diaphragm with a top and bottom portion thereof partially cut off.

5. A stereoscopic retinal camera comprising:
    an illumination system including a photographing light source and an observation light source for respectively transmitting a photographing light and an observation light along a common illumination light path, wherein the observation light source includes an infrared filter;
    means for focusing the photographing light and the observation light transmitting along the common illumination light path onto a fundus of an examinee's eye to be stereoscopically photographed;
    a photographing diaphragm having two apertures for dividing photographing light and observation light reflected by the fundus into stereoscopic light beams, wherein each aperture of the photographing diaphragm has a longer vertical length than width, and is substantially symmetrical in shape about a vertical central axis;
    means for supplying the stereoscopic light beams to an observation optical system and a photographing optical system;
    an infrared light observation device disposed in the observation optical system to receive the stereoscopic light beams;
    a photographing device disposed in the photographing optical system to receive the stereoscopic light beams;
    whereby the fundus may be photographed stereoscopically with the photographing device without mydriatica.

6. A stereoscopic retinal camera according to claim 5, wherein the infrared light observation device comprises a television camera sensitive to infrared radiation and a television monitor.

7. A stereoscopic retinal camera according to claim 6, further comprising a display means for displaying separately a pair of observation images on the television monitor.

8. A stereoscopic retinal camera according to claim 7, wherein the apertures comprise a longitudinal ellipse, drum-like shape.

9. A stereoscopic retinal camera comprising:
    illumination optical system for illuminating a fundus to be photographed with a luminous flux comprising at least one of and observing illumination light and a photographing illumination light;

photographing optical system for transmitting the luminous flux reflected by the fundus onto a photographing film;

observation optical system for transmitting the luminous flux reflected by the fundus onto an imaging device;

said photographing optical system and said observation optical system partially sharing a common light path which comprises a photographing diaphragm, said photographing diaphragm including a pair of apertures to divide the luminous flux reflected by the fundus into two stereoscopic light beams for stereoscopic observation through said observation optical system and for stereoscopic photographing through said photographing optical system; wherein each aperture of the photographing diaphragm are shaped like a drum which has a longer vertical length than width, and is substantially symmetrical in shape about a vertical central axis.

10. A stereoscopic retinal camera according to claim 9, wherein said photographing diaphragm is disposed in a substantially conjugate relationship with a pupil of examinee's eye through an objective lens.

11. A stereoscopic retinal camera according to claim 9, wherein the apertures of the photographing diaphragm have an area equal to or wider than same of the luminous flux of 1.5 mm in diameter.

12. A stereoscopic retinal camera according to claim 9, wherein a center distance between both apertures of the photographing diaphragm keeps a stereobase distance between bases through which a right stereo luminous flux and a left stereo luminous flux pass respectively, and wherein the outside distance between both apertures of the photographing diaphragm is in accordance with the small pupil diameter of the examinee's eye when the image thereof is projected on said photographing diaphragm.

13. A stereoscopic retinal camera according to claim 9, wherein said illuminating optical system comprises an infrared light transmitting filter for transmitting only infrared light by removing a visible light element from the observing illumination light, and wherein the imaging device disposed in said observation optical system comprises a TV camera imaging element sensitive to infrared light.

14. A stereoscopic retinal camera according to claim 1, wherein the apertures comprise a longitudinal ellipse, drum-like shape.

* * * * *